(12) United States Patent
Drake et al.

(10) Patent No.: US 7,517,355 B2
(45) Date of Patent: Apr. 14, 2009

(54) METHOD OF SUPPORTING AND/OR APPLYING PARTICULATE MATERIALS

(75) Inventors: James Franklin Drake, Minneapolis, MN (US); Lynn R. Skow, North Branch, MN (US)

(73) Assignee: Medafor, Incorporated, Minneapolis, MN (US)

( * ) Notice: Subject to any disclaimer, the term of this patent is extended or adjusted under 35 U.S.C. 154(b) by 487 days.

(21) Appl. No.: 11/222,444

(22) Filed: Sep. 8, 2005

(65) Prior Publication Data

US 2007/0054040 A1     Mar. 8, 2007

(51) Int. Cl.
*A61B 17/08*    (2006.01)
*A61D 1/00*    (2006.01)

(52) U.S. Cl. .................................... 606/213

(58) Field of Classification Search ............... 606/213; 514/54; 602/48
See application file for complete search history.

(56) References Cited

U.S. PATENT DOCUMENTS

| | | | |
|---|---|---|---|
| 3,081,698 A | 3/1963 | Childress et al. | 101/129 |
| 3,166,432 A | 1/1965 | Gundlach | 430/120 |
| 4,337,303 A | 6/1982 | Sahyun et al. | 430/11 |
| 4,512,057 A * | 4/1985 | Laing et al. | 15/320 |
| 4,698,907 A | 10/1987 | Soszek | 29/846 |
| 5,817,374 A | 10/1998 | Detig | 427/466 |
| 5,817,381 A | 10/1998 | Chen et al. | 428/34.8 |
| 6,060,461 A | 5/2000 | Drake | 514/54 |

OTHER PUBLICATIONS

U.S. Appl. No. 10/164,365, filed Dec. 4, 2003, Drake et al.

* cited by examiner

*Primary Examiner*—Vy Q Bui
(74) *Attorney, Agent, or Firm*—Patterson, Thuente, Skaar & Christensen, P.A.

(57) ABSTRACT

Masses of particles are structurally supported by the application of vacuum through a support surface having holes thereon that are smaller than the average diameter of the particle mass that is to be supported. The reduced pressure structurally supports particles on the support surface. The mass of particles tends is so well supported that it tends retain its shape unless additional forces are applied. The system comprises the vacuum applicator (e.g., pump), a vacuum carrying system and the support surface. When a mass of particles is supported on the support surface under vacuum, the particles can be carried to a target surface, the mass of particles pressed against the target surface, the mass conforming to the target surface, and the vacuum reduced or stopped, depositing the particle mass onto the surface in excellent shape compliance with that surface.

22 Claims, 4 Drawing Sheets

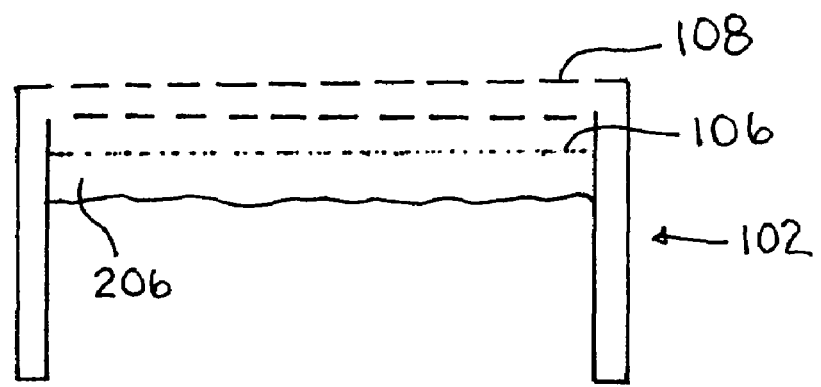
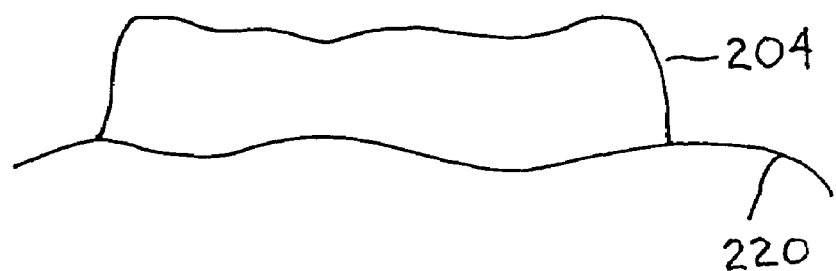
FIG. 4

METHOD OF SUPPORTING AND/OR APPLYING PARTICULATE MATERIALS

BACKGROUND OF THE INVENTION

1. Field of the Invention

The present invention relates to the field of particle control, particle application and to processes where particles can be supported during application and released from support.

2. Background of the Art

The application of particles to surfaces has been performed in many different ways in many different disciplines. Early paint is in fact often comprised the manufacture of a slurry of particles in a volatile (water) liquid carrier, the application of the slurry to a surface and the subsequent drying of the slurry s applied. Coloration of tiles often included glazes of particles that were applied and fired to surfaces.

Many modern technologies find the application of particles to be essential to manufacturing and performance systems. A whole new field of technology has developed revolving around the field of ultrasmall particles, nanoparticles.

Silk screen printing is one of the oldest graphic arts technologies (besides manual deposition of pigments or dyes to a surface) still in commercial use. The process was believed to have been originated by the ancient Chinese, using silk screens to deposit colorant fluids (e.g., inks) through the screen onto a surface. The technology is still used commercially today, not only for imaging, but also for manufacture of detailed patterns for circuitry, conductors, adhesives and the like. Window defrosters and antennae on car windows are sometimes still made by the process.

Few dry powder screening processes have been known to provide sufficient benefits to succeed commercially. It is believed that early Chinese artists may have manually brushed dry powder through the silk screens onto various surfaces to which the powders would adhere.

U.S. Pat. No. 4,698,907 teaches processes for the application of patterns of dry metallic powders. The processes use electrophotography, electrically charged drums, latent charge images (e.g., electrography), or dielectric webs, with metal powders applied as toners from brushes or cascade development applicator systems. It is disclosed that the metal powder is to be coated with a thin dielectric layer so that it may be electrically charged and transferred.

U.S. Pat. No. 3,166,432 teaches that electrically conducting toner particles may be applied by induction development. Indeed, many commercial copying or imaging systems use dry toner powders (usually defined as having less than 10% by weight volatile materials in fresh materials) as the toning agents. These toners often comprise a blend or other physical association of colorant (e.g., pigment or dye), binder, and charge control agent. These particles tend to be very thin layers of particles (even monolayers in may cases) when they are applied, described in Schein, Electrophotography and Development Physics, Springer Vertag, Berlin 1988, P. 180. The application of multiple layers or thick layers of toner materials may require the use of special receptor surfaces with coatings that are receptive to larger volumes of materials (e.g., U.S. Pat. No. 4,337,303, Sahyun et al.).

U.S. Pat. No. 3,081,698 described an electrostatic stencil screen printing process. Contact free printing was performed on delicate or rough surfaces by moving a dry resinous material through the openings of a stencil mask by electrostatic forces. In all cases, the toner used was a dry resinous material that could be triboelectrically charged, and a powder cloud of the material was mechanically created. In FIG. 5, the particles are apparently being suspended by air movement. The charged toner particles were projected through the mask or stencil at a relatively distant target/receptor (e.g., paper being separated from the stencil by an air gap).

U.S. Pat. No. 5,817,374 (Detig) describes that particles are applied to the surfaces of materials, especially in the form of discontinuous or patterned coatings on the surfaces of sheet materials by a process comprising the steps of: a) providing a support, b) placing a bed of non-adhered particles on the support, the particles being capable of being moved by an electric field of less than 100 KV/cm, c) placing a mask with a first and second surface over the bed of non-adhered particles, the mask having holes which pass from the first to the second surface, the first surface facing the bed of non-adhered particles without the mask touching the bed of non-adhered particles, the holes in the mask having a size which would allow passage of individual particles from the bed of non-adhered particles through the holes, d) placing a receptor material capable of at least temporarily retaining an electric charge adjacent to the second surface of the mask, which second surface faces away from the bed of non-adhered particles, e) applying an electrical charge to the receptor material which is at least temporarily retained by the receptor material, f) applying an electrical field between the mask and the support, the electrical field being of at least sufficient strength to cause individual particles from the bed of non-adhered particles to move off the first substrate and impact the mask, g) allowing some of the individual particles which move off of the support to enter the holes in the mask and contact the receptor material, and h) the contract by individual particles to the receptor material causing at least some of the particles contacting the receptor material to adhere to the receptor material at least by charge attraction of the individual particles to charge on the receptor material.

U.S. patent application Ser. No. 10/164,365, filed May 31, 2002 describes A delivery system is described for the delivery of flowable medicinal, therapeutic or medicine materials. The delivery system comprises a strip having flowable material contained and restrained therein. A removable seal is provided, so that when the removable seal is removed, the flowable material will flow from a storage area onto the site selected for treatment. The removable seal may be provided with additional features such as absorbent coatings, or additional disinfectants coatings useful in preparing the wound surface to receive the flowable wound treatment material. The delivery system may be contained in an adhesively securable element such as a bandage, band-aid, applique', wrap, patch, or the like. The system may be secured to a patient along a limited amount of the edge of the system, the removable seal removed, causing the contained material to flow, and additional edges of the system secured to the patient. The securing of the system may be effected by adhesives, such as activatable adhesives (e.g., solvent or water activated adhesive) or pressure-sensitive adhesive. A preferred composition is a system, article and method for the enhancement of clotting in wounds with extravascular blood flow, especially where the surface of the tissue has been broken. The composition consists of biotolerable, porous particulates (with pores chosen of the appropriate size for the effect desired) applied to the surface of a wound with liquid blood thereon. The porous nature of the particulate material, either free-flowing or packaged or restrained on or in a surface, enhances clotting. Chemical or biochemical agents, such as additional clotting agents, therapeutic agents, antibiotics, clot strengthening agents (such as fibrous structural materials), and the like may optionally be included on, with or within the porous particles. Where the porous particle clotting agents are used with animals, materials which are mildly repellant to the animal patient (without being toxic) may be included within the applied particle material to assure that the animal will not tamper with the wound during healing, a common problem with veterinary treatments. The particles may comprise such diverse materials as organics, metallics, inorganics, ceramics, and the like, both natural and artificial. It is generally preferred that the pore size distribution lies within a general range, and this range may vary from animal to animal and condition to condition, but generally falls within about 0.5-1000 NM or 1 to 1000 nm, or about 5 to 500 nm, depending upon the particular use. Preferred particles are those applied for the purposes of U.S. Pat. No. 6,060,461.

Additional and controllable methods for the carrying of particles and the application of particles to other surfaces are desired, including the application of particles to patients during medical procedures.

SUMMARY OF THE INVENTION

Masses of particles are structurally supported by the application of vacuum through a support surface having holes thereon that are smaller than the average diameter of the particle mass that is to be supported. The reduced pressure on one side of the support surface causes a fluid flow (usually a gas, and most often air) or pressure differential across the mass of particles such that the particles are structurally supported on the support surface. The mass of particles tends is so well supported that it tends retain its shape unless additional forces are applied. With many particle masses of modest dimensions (e.g., nanometer particles to 100 micrometer particles), the shape is supported in masses having a maximum thickness of seven about 1-2 cm even when the support surface is positioned vertically so that the full weight of gravity is directed perpendicularly against the height of the supported mass of particles.

The system comprises the vacuum applicator (e.g., pump), a vacuum carrying system (e.g., tubes or pipes), and the support surface. When a mass of particles is supported on the support surface under vacuum, the particles can be carried to a target surface, the mass of particles pressed against the target surface, the mass conforming to the target surface, and the vacuum reduced or stopped, depositing the particle mass onto the surface in excellent shape compliance with that surface. By controlling the degree of reduction of the vacuum, the amount or mass of particles transferred can be adjusted or controlled.

BRIEF DESCRIPTION OF THE FIGURES

FIG. 3A shows a particle mass supported on a filter.

FIG. 4 shows a mass of particles being deposited from a reduced vacuum support surface after being pressed against a target surface, conforming thereto, and having the vacuum pressure reduced.

DETAILED DESCRIPTION OF THE INVENTION

Particles in a wide range of sizes can be supported, carried and transferred to and from a support surface. The support surface has to have holes that are smaller than the average diameter of the particles in a particle mass that is being supported on the support surface, at least those particles that are in direct contact with the particle support surface. For example, if the holes in the particle support surface were X microns, particles of, for example, 1.1X microns could be supported directly against the support surface and smaller particles, such as 0.9X particles could be supported on the surface of the stabilized mass of 1.1X micron particles.

The support surface has a significant percentage of its surface to be in contact with the particles open, with holes of sufficient size to allow passage of gas (e.g., generally air) through the holes at a sufficient rate to support a differential pressure across the support surface that can retain particles on the surface having a higher gas pressure thereon. There are numerous methods of controlling the hole size on the support surface, such as providing holes in a plate of the appropriate size, having adjustable overlying plates with holes in at least two overlying plates that may be respectively adjusted to control the effective hole size. A simple methodology uses a support plate with relatively large hole(s) therein, but a support structure (e.g., beams, hatching, etc.) extending over a portion of the large hole(s), and placing a screen over the hole(s), which screen is supported itself by the support structure internal to the support plate. For example, the support plate may have a 5 cm diameter hole thereon, with a grid of 5×5 stiff 1.0 mm wires across the hole. A screen may be cut to fit the 5 cm diameter hole and lie over the grid, and be supported thereby.

Figure 1:
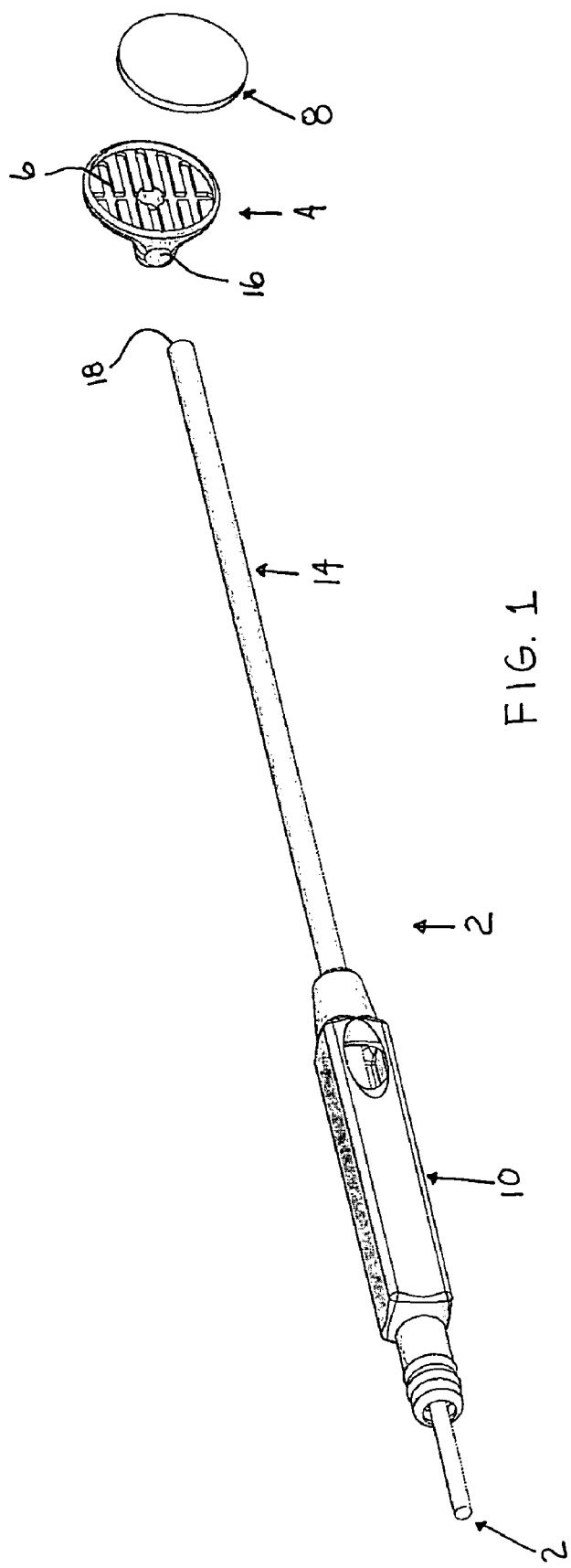
FIG. 1 shows a first embodiment of a particle applicator with perpendicularly extending support comprising an open plate and filter.

Reference to the figures will assist in a further understanding of the technology described herein. FIG. 1 shows a first embodiment of a particle applicator 2 with perpendicularly extending support 4 comprising an open plate 6 and filter 8. The applicator 2 has a handle portion 10 into which a vacuum source connection 12 is provided. The reduced pressure of the vacuum is transmitted along the applicator by tube arm 14. The end 18 of the arm 14 is shown with a connecting port 16 on the support 4. The plate 6 is sufficiently open to allow air flow back through the support 4 and back through the tube arm 14. The porosity of the filter 8 will be the main limiting factor of the air pressure differential applied to the base of particles (not shown) that are contacted with the filter during vacuum application. The connection between the port 16 and the end 18 of the arm 14 may swivel by having a swivel, air-tight connecting link.

Figure 2:
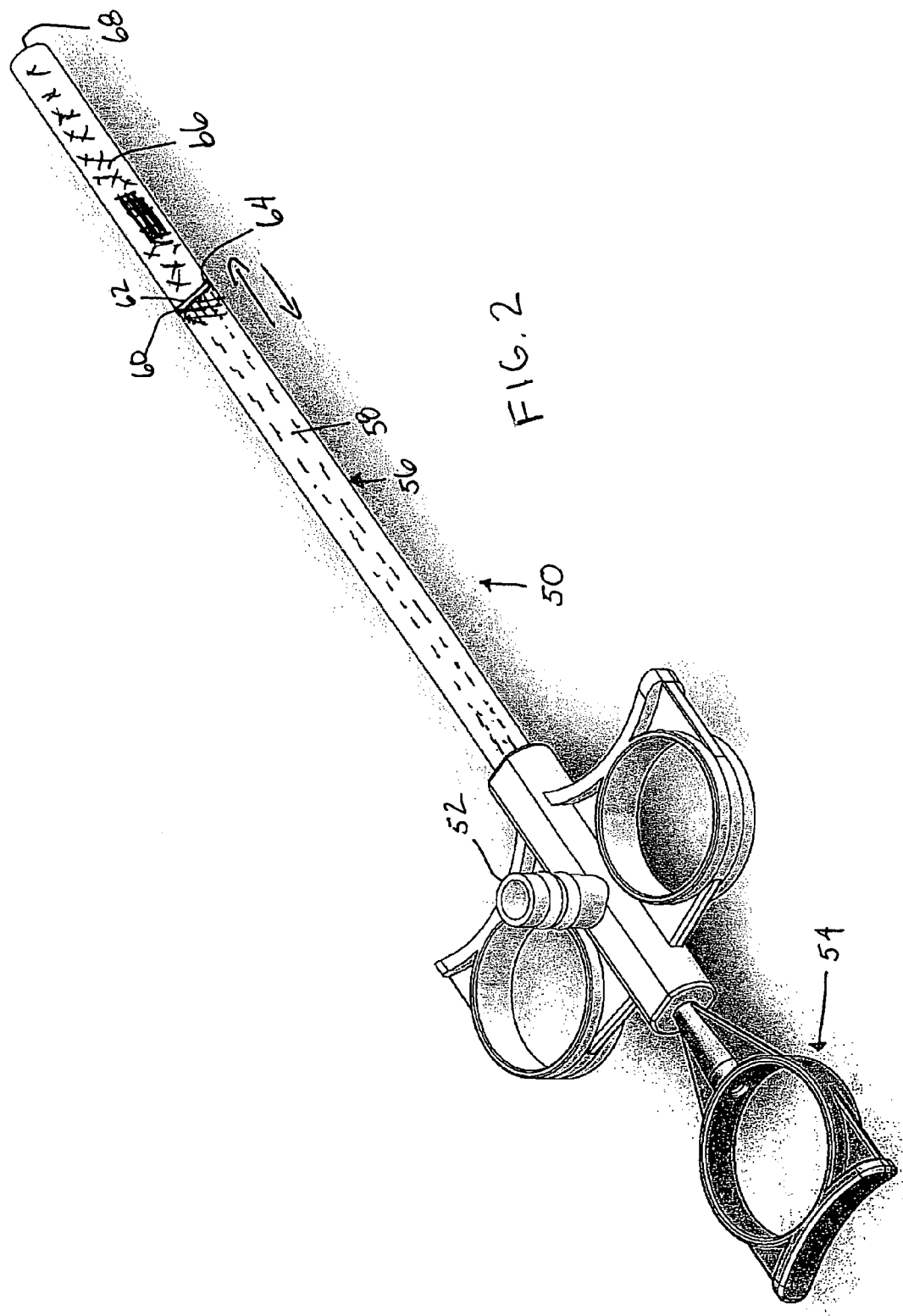
FIG. 2 shows an alternative applicator structure.

FIG. 2 shows an alternative applicator structure 50. This structure 50 has a vacuum port 52 to which a vacuum connection (e.g., tube, not shown) is attached. A finger or thumb motivated attachment 54 drives a shaft 58 through the vacuum shaft 56. At the end of the shaft 58 is a fitted end 60 that is open for facile gas flow therethrough. The porous fitted end 60 supports and filter 62 (optional), and the fitted end 60 and the filter 62 form a relatively pressure secure fit between the fitted end 60, filter 62 and the interior surface 62 of the vacuum shaft 56.

The filter 62 is shown in a position within the vacuum arm 56 and is supporting a volume of particles 66 such that if the end of the applicator 68 were pointed down, no particles 66 would flow out of the end 68 of the arm 56. Reducing pressure differential (reducing the vacuum either by a control (not shown) in the applicator or by reducing the vacuum provided to vacuum port 52) reduces the supporting forces on the particles such that as the mass of particles 66 is pressed out the end 68 of the arm 56, less particle mass can be supported and more particle mass can be delivered.

FIG. 3A shows a particle mass 104 supported on a filter 106 on an applicator head 102. The applicator head 102 has an internal plate 108 that supports the filter 106 that supports the particle mass 104. External air pressure A and B presses on the particle mass 104 due the driving force of the reduced pressure (vacuum source) C. The air (gas) flows along paths a within the particle mass 104 to support the particles against the filter 106. Depending upon the differential pressure between A and C, the density of the particles, the size of the particles, and other apparent parameters, the size of the mass of the particles may vary significantly. With ideal spherical particles that provide a well defined pathway between the particles and throughout the entire particle mass 104, a height of the particle mass has been established for 5-100 micron particles at as much as 5 cm, with a 0.25 atmosphere (190 mm Hg) pressure differential. Lesser pressure differentials and greater pressure differentials can be used to alter the height of particles that can be supported. For example, pressure differentials of between 50 and 760 mm Hg may be used to support particles, preferably between 50 and 700 mm Hg.

Figure 3:
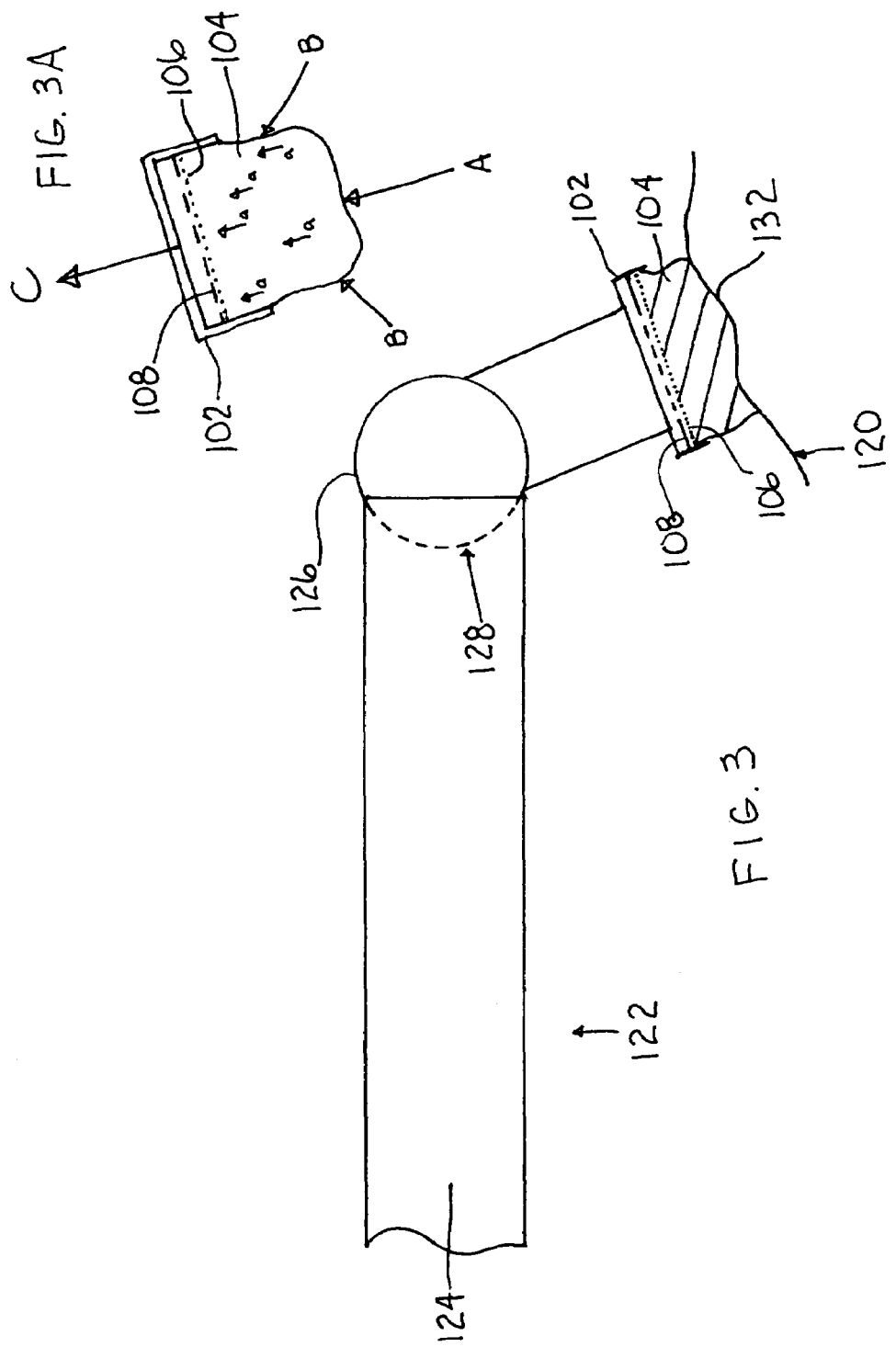
FIG. 3 shows a mass of particles on a vacuum support surface being pressed against a target surface and conforming thereto.

FIG. 3 shows a mass of particles 104 on a vacuum support head 102 being pressed against a target surface 120 and conforming thereto. The vacuum arm 122 is connected to a vacuum source 124 and the reduced pressure is connected to the applicator head 102 through a swivel ball 126 engaged with the arm 22 with a porous surface 128 transmitting air pressure through it. As can be seen, the mass of particles 104 supported on the filter 106 which is in turn supported by a porous plate 108 conforms to the surface shape 132 of the target surface 120.

FIG. 4 shows a mass of particles 204 being deposited from an applicator head 102 having an internal porous support surface 108 carrying a filter 106 thereon. The applicator head 102 has been withdrawn from the target surface 220 after the vacuum has been reduced. The reduced vacuum would no longer support the original entire particle mass (a sum of 204 and 206), so that upon withdrawal of the applicator head 102 a desired amount of particle mass 204 is left on the target surface 220 and a remaining portion of particle mass 206 is carried under pressure differential away from the target surface 220.

The system and method of the presently described technology may be used with a wide range size and density of particles in a wide range of technologies. Particles may be applied for decorating purposes, structural repair purposes, protective covering application, powder molding processes and medical treatments. Even though the particles may be applied for all of these varied purposes, the primary discussion will be directed towards medically applicable particles and their deposition. This emphasis is not intended to limit the practice of the invention, but rather is intended to provide specific embodiments within the generic concepts described. The fact that particles with medical functions may be picked up, carried and deposited by the described physical process technology and systems does not imply that only particles with that function may be so treated.

As repeatedly noted herein, the actual parameters of operation of the system can vary over a significant range of particles sizes and pressures. The pressure should usually be considered in terms of differential pressures between the outer surface of the particle mass and the inner surface of the particle mass supported on the support plate. It may be generally assumed that the outer pressure is approximately atmospheric pressure (the process may be performed in controlled environments, including reduced pressure or increased pressure operating environments), so the capability of the vacuum source should generally be considered with respect to ability to provide the differential versus atmospheric pressure. With finer particles (e.g., less than 1 micron, less than 5 microns), relatively low pressure differentials (e.g., about 50 mm Hg) are sufficient to support meaningful thicknesses of particles, for example at least 0.5 mm. With larger average diameter particles, for example 5-50 microns, somewhat greater pressure differentials are required, at least in part because there will be heavier particles and greater air flow over the particles, for example, 50-100 mm Hg. With still larger particles, for example, 50-100 microns, still larger pressure differentials are needed to support meaningful thicknesses of particle masses, for example, 75-200 mm Hg. Higher pressure differentials, as previously noted, can always be tolerated, but require more expensive equipment.

A preferred composition for application to the surface of broken or otherwise damaged tissues, especially where liquids or blood is present within the damaged area or wound comprises bio-tolerable, porous particulates (with pores chosen of the appropriate size for the effect desired) applied to the surface of a wound with liquid blood thereon. The porous nature of the particulate material, either free-flowing or packaged or restrained on or in a surface, enhances clotting. Chemical or biochemical agents, such as additional clotting agents, therapeutic agents, antibiotics, clot strengthening agents (such as fibrous structural materials), and the like may optionally be included on, with or within the porous particles. Where the porous particle clotting agent are used with animals, materials which are mildly repellant to the animal patient (without being toxic) may be included within the applied particle material to assure that the animal will not tamper with the wound during healing, a common problem with veterinary treatments. The particles may comprise such diverse materials as organics, metallics, inorganics, ceramics, and the like, both natural and artificial. It is generally preferred that the pore size distribution lies within a general range, and this range may vary from animal to animal and condition to condition, but generally falls within about 0.5-1000 NM or 1 to 1000 nm, or about 5 to 500 nm, depending upon the particular use.

A composition which may be used for the enhancement of the clotting of blood in animals, including mammals, avians and reptiles comprises porous particulate material which is applied to the wound when there is blood in a liquid or only partially clotted state (e.g., where it may wet the particles). The particles may be applied to the wound area either as a free flowing powder of the particles, a dry spray of particles, a moist spray or aerosol of the particles, as an association of particles in or on a carrier (such as a web, tape, fabric, foam, reticulated foam, or film), and may optionally contain conventional clotting agents with the particles. The particle application should enable direct contact of the particles with the flow of blood, preferably without any non-clotting intermediate film or material between the blood at the site of the wound and the clotting particles. For example, the use of the particles on the surface of a film with that surface facing the wound would be acceptable. In that orientation, the blood would clot on the wound site. On the other hand, where a fairly thick, but porous film was used, and the blood flowed through the pores of the film (e.g., greater than 0.1 mm thickness) to reach the porous clotting particles on a backside of the film, the clot would not occur on the wound site. That would not be the most advantageous location for the clot enhancing particles. An intermediate and acceptable structure would be to have the particles located within a thin, light fibrous mass so that as the particles enhanced clotting, the fibers would remain within the region of clotting and strengthen the clot. The fibers could also be used to assist in carrying optional materials (e.g., antibiotics) to the wound site. One type of desirable materials of this last format would have a woven, non-woven or knitted fibrous sheet (e.g., less than 1 mm in thickness, e.g., 0.05 to 0.5 mm, or 0.1 to 0.5 mm thick) with the fabric having a porosity of at least 30% (e.g., 30-95%, 40-95%, or 50-95% porosity), with at least a portion of the porosity filled with the clot enhancing particles described for use in the practice of the present invention. The particles may be carried within the structure of the fabric or bonded to the fibers, filaments, or yarns of the fibrous material (taking care not to completely fill the pores of the particles with any binder used).

The particles for this particular medical application may generally have a size of from about 1 to 1000 micrometers, or 1 to 500 micrometers, but the size may be varied by one ordinarily skilled in the art to suit a particular use or type of patient and depending on the ability of a carrier to support the particles with their optional selection of sizes. Examples of specific materials useful in the practice of the present invention comprise porous materials from within the classes of polysaccharides, cellulosics, polymers (natural and synthetic), inorganic oxides, ceramics, zeolites, glasses, metals, and composites. Preferred materials are of course non-toxic and are provided as a sterile supply. The polysaccharides are preferred because of their ready availability and modest cost. The porous particulate polysaccharides may be provided as starch, cellulose and/or pectins, and even chitin may be used (animal sourced from shrimp, crab and lobster, for example). Glycosaccharides or glycoconjugates which are described as associations of the saccharides with either proteins (forming glycoproteins, especially glycolectins) or with a lipid (glycolipid) are also useful. These glycoconjugates appear as oligomeric glycoproteins in cellular membranes. In any event, all of the useful materials must be porous enough to allow blood liquid and low molecular weight blood components to be adsorbed onto the surface and/or absorbed into the surface of the particles. Porosity through the entire particle is often more easily achieved rather than merely etching the surface or roughening the surface of the particles.

Ceramic materials may be provided from the sintering, or sol-gel condensation or dehydration of colloidal dispersions of inorganic oxides such as silica, titanium dioxide, zirconium oxide, zinc oxide, tin oxide, iron oxide, cesium oxide, aluminum oxide and oxides of other metal, alkaline earth, transition, or semimetallic chemical elements, and mixtures thereof. By selection of the initial dispersion size or sol size of the inorganic oxide particles, the rate of dehydration, the temperature at which the dehydration occurs, the shear rate within the composition, and the duration of the dehydration, the porosity of the particles and their size can be readily controlled according the skill of the ordinary artisan.

With regard to cellulosic particles, the natural celluloses or synthetic celluloses (including cellulose acetate, cellulose butyrate, cellulose propionate, etc.) may be exploded or expanded according to techniques described in U.S. Pat. No. 5,817,381 and other cellulose composition treating methods described therein which can provide porous particles, fibers and microfibers of cellulose based materials. Where the porous materials, whether of cellulose or other compositions, have a size which may be too large for a particular application, the particles may be ground or milled to an appropriate size. This can be done by direct mortar and pestle milling, ball milling, crushing (as long as the forces do not compress out all of the porosity), fluidized bed deaggregation and size reduction, and any other available physical process. Where the size of the raw material should be larger than the particle size provided, the smaller particles may be aggregated or bound together under controlled shear conditions with a binder or adhesive until the average particle size is within the desired range.

Porosity may be added to many materials by known manufacturing techniques, such as 1) codispersion with a differentially soluble material, and subsequent dissolution of the more soluble material, 2) particle formation from an emulsion or dispersion, with the liquid component being evaporated or otherwise removed from the solid particle after formation, 3) sintering of particles so as to leave porosity between the sintered or fused particles, 4) binding particles with a slowly soluble binder and partially removing a controlled amount of the binder, 5) providing particles with a two component, two phase system where one component is more readily removed than another solid component (as by thermal degradation, solubilization, decomposition, chemical reaction such as, chemical oxidation, aerial oxidation, chemical decomposition, etc.), and other known process for generating porosity from different or specific types of compositions and materials. Where only surface porosity is needed in a particular clot promoting format, surface etching or abrasion may be sufficient to provide the desired surface porosity.

A particularly desirable and commercially available material comprises polysaccharide beads, such as dextran beads which are available as Sephadex™ beads from Pharmacia Labs. These are normally used in surgery as an aid to debridement of surfaces to help in the removal of damaged tissue and scar tissue from closed wounds. The application of this type of porous bead (and the other types of porous beads to open wounds with blood thereon) has been found to promote hemostasis, speeding up the formation of clots, and reducing blood loss and the need for continuous cleaning of the wound area. Bleeding from arteries, veins and small capillaries, soft tissue, organs (e.g., liver, kidney, lungs and spleen) can be effectively managed, reduced and eliminated in most cases by application of the particles or beads according to the present invention.

The porous particles or porous beads may be directly applied to surfaces or held in place by pressure on the application device, and shaped to the surface to which the particles are being applied. The vacuum pressure may also be of value in drawing liquid from the target area of application into the particle mass. The beads or particles may be free flowing or be supported on a temporary surface (e.g., flat surface or container) or in a containment system. For example, the particles may be adhered to the surface of a sheet or film which is applied to the collection surface of the applicator (e.g., contacted, secured, affixed or otherwise placed into a position where the applicator head can be contacted with a sufficient mass of particles that can distribute themselves over the surface where the vacuum is presented through the plate or filter. The particles may also be provided in a form where the porous particles or porous beads may be interspersed with fibers, filaments or other particles in a free floating mass that can be supported by the vacuum head. The terms particles and beads are not intended to denote any substantive difference in size, shape or performance of materials and are not asserted as having any distinct differences within the practice of the present invention, but are merely alternative terms. The use of only one term does not intend that the other term is not equally applicable in the context in which the one term is used. The porous particles and porous beads may also be provided as part of a patch system, with a fibrous network associated with the particles to provide a high level of structural integrity and strength to the applied assembly over the wound, even before clotting has occurred. This would be particularly appropriate where the assembly was being used as a stitch replacement or true wound closure system rather than only promoting clotting.

The porous particles may easily be associated with or carry additional, but optional, clotting or wound treating materials or ingredients. For example, it would be desirable to provide the porous particles with antibiotics, antifungal agents (especially where application may be in a tropical environment), topical pain reducing medication, pharmaceuticals, anti-inflammatants, tissue enzyme inhibitors (e.g., epsilon aminocaproic acid, to reduce tissue enzyme production that would weaken the blood clot), and the like. Existing materials which promote clotting or control bleeding would be particularly, such as thrombin, fibrinogen, aprotinin, fibronectin, and factor XIII. However, one of the advantages of the materials which may be used (excluding those derived from animals) is that they are not made from animal components as are the typical clotting or wound treatment materials noted above. As there is always a potential for animal based materials being a source of infection themselves (e.g., viral infection, spongiform encephalopathy, allergic reactions, etc.), the avoidance of animal based products, which can be easily accomplished in the practice of the present invention, is desirable.

The preferred polysaccharide components for the porous particles and porous beads of the present invention may often be made from cross-linked polysachharides, such as cross-linked dextran (poly[beta-1,6-anhydroglucose]). Dextran is a high molecular eight, water-soluble polysaccharide. It is not metabolized by humans, is non-toxic, and is well tolerated by tissue in most animals, including most humans. There have even been extensive use of solubilized dextrans as plasma substitutes. The Sephadex™ beads specifically mentioned in the description of particularly useful polysaccharides comprise dextran crosslinked with epichlorihydrin. These beads are available in a variety of bead sizes (e.g., 10 to 100 micrometers, with a range of pore size. It is believed that pore sizes on the order of from 5 to 75% of volume may be commercially available and can be expanded to from 5 to 85% by volume or manufactured with those properties from amongst the type of beads described above. The sizes of the pores may also be controlled to act as molecular sieves, the pore size being from 0.5% or 1 to 15% of the largest diameter of the particles or beads. The Sephaex™ beads are promoted as having controlled pore sizes for molecular weight cutoff of molecules during use as a sieve, e.g., with cutoff molecular being provided at different intervals between about 5,000 Daltons and 200,000 Daltons. For example, there are cutoff values specifically for molecular weight sizes of greater than 75,000 Daltons. This implies a particle size of specifically about 10 to 40 microns. These beads will rapidly absorb water, swelling to several times their original diameter and volume (e.g., from 1.2 to as much as five times their volume).

EXAMPLE

A vacuum pump can be provided that supports a continuous and smooth application of a differential pressure of 200 mm Hg was connected to a vacuum tube attached to an application head having properties described herein. A head construction could comprise a two centimeter diameter circular plate with a 2 mm vertical lip around the edges. A mesh screen, having holes sizes averaging less than 50 microns would be placed within the lip. The vacuum pump would be turned on, and the vacuum applicator head (the filter) would be brought into contact with a pile of 200 micron Sephadex™ beads. This would cause a mass of about 1 cm of beads to be lifted from the mass of beads. The use of a probe against the surface of the mass supported by the filter would disturb the shape of the supported mass of particles, but would not cause a significant percentage of particles to fall from the mass unless the probe were used to pick and lift particles from the supported mass.

The following part of this surgery was done by direct powder application (pouring) or the Sephadex™ particles, but could have been readily accomplished by pressing vacuum supported powder onto the open wound area. Surgery to remove the claws of domestic cats can result in considerable bleeding unless precautions are taken to prevent this complication. Generally, following removal of the claw at the first joint, the artery leading to the tip of the digit is sealed by suturing, application of surgical glues, or other available means. Despite these conventional treatments, considerable bleeding often follows removal of the claws, often requiring additional veterinary treatment. Application of cyanoacrylate-based adhesives to control such bleeding often results in inflammation and development of granulomatous deposits as a complication. The following examples show the usefulness of the practice of the present invention within the realm of cat declawing surgery.

A domestic cat was anesthetized and prepared for de-claw surgery in a standard manner. Preparation of the patient included the application of a tourniquet to prevent bleeding during the procedure. Following removal of the claw, the remaining cavity was filled with dry, free-flowing Sephadex™ G-25 powder (Pharmacia, Inc.), a cross-linked dextran bead having an average particle size of 20 to 80 micrometers, with a molecular weight size exclusion of 3,000 Daltons. The powder was applied to the cavity of the wound with a plastic dropper (e.g., eye dropper), the powder firmly pressed into the wound cavity, and firm pressure maintained on the powder in the wound cavity for about one minute. The efficacy of the procedure was tested by loosening the tourniquet and watching for any bleeding from the fresh wound. The procedure was repeated for each of the claws on each of the four feet of the cat. None of the wounds showed any significant blood loss. The attending veterinarian judged the procedure to be equal to or better than the use of surgical glue for controlling bleeding during the procedure. Following the surgery, the cat recovered normally, with no signs of inflammation or granulomatous lesions at the surgical site.

What is claimed:

1. A method of applying particulates to a wound comprising:
   providing at a location a mass of particulates having an average particle diameter;
   providing a porous surface with pores having a shortest average dimension of pore openings, the shortest average dimension of pore openings being less than the average particle diameter,
   providing a gas pressure on a first side of the porous surface;
   providing a lesser gas pressure on a second side of the porous surface to create a pressure differential across the porous surface;
   contacting the first side of the porous surface with the mass of particulates;
   removing the porous surface from the location; and
   carrying a portion of the mass of particulates on the first side of the porous surface to a wound by pressure established by the differential an air flow through the portion of the mass of the particulates while carrying the portion of the mass of particulates, the air flow being.

2. The method of claim 1 wherein the portion of the mass of particles comprises a layer of particles having an average of at least 20 particles thickness in the portion of the mass of particles across the porous surface.

3. The method of claim 1 wherein the thickness of the portion of the mass of particles comprises at least 1 mm in thickness.

4. The method of claim 1 wherein the average particle diameter is less than 10,000 microns.

5. The method of claim 1 wherein the average particle diameter is less than 1,000 microns.

6. The method of claim 1 wherein the average particle diameter is between 1 and 1,000 microns.

7. The method of claim 2 wherein the pressure differential is at least 50mm Hg.

8. The method of claim 3 wherein the pressure differential is at least 50 mm Hg.

9. The method of claim 3 wherein the pressure differential is at least 100 mm Hg.

10. The method of claim 3 wherein the pressure differential is at least 100 mm Hg.

11. The method of claim 8 wherein the porous surface comprises a filter on a support.

12. The method of claim 9 wherein the porous surface comprises a filter on a support.

13. The method of claim 10 wherein the porous surface comprises a filter on a support.

14. The method of claim 1, wherein after the portion of the mass of particles is carried to the wound, the pressure differential is reduced, the porous surface is moved away from the wound and at least a second portion of the portion of particle mass is left against the wound.

15. The method of claim 14 wherein application of the particles comprises a method for enhancing the formation of clots on a wound of an animal where blood is present comprising the steps of applying porous particles of dimensions of from about 0.5 to 1000 micrometers as the second portion of particle mass to at least a portion of said wound where blood is present in said wound, allowing said porous particles to remain in contact with said blood in said wound while clotting initiates in said wound.

16. The method of claim 15 wherein said porous particles having molecular sieve cutoff values between about 5,000 Daltons and 200,000 Daltons.

17. The method of claim 14 wherein said pores comprise from 5 to 35% of the volume of the porous particles.

18. The method of claim 14 wherein said particles are applied to said wound with blood as free-flowing particles.

19. The method of claim 14 wherein said porous particles are applied to said wound along with another material selected from the group consisting of antibiotics, antifungal agents, topical pain reducing medication, pharmaceuticals, anti-inflammatants, and tissue enzyme inhibitors.

20. The method of claim 14 wherein the wound comprises broken soft tissue within a human body.

21. A method for enhancing the formation of clots on a wound of an animal where blood is present comprising the steps of applying porous particles according to the method of claim 14, the particles having average diameter dimensions of from about 0.5 to 1000 nanometers to at least a portion of said wound where blood is present, allowing said porous particles to remain in contact with said blood while clotting initiates.

22. The method of claim 1,the method further comprising utilizing said differential pressure to draw blood present at the wound into the mass of particles.

\* \* \* \* \*

UNITED STATES PATENT AND TRADEMARK OFFICE
CERTIFICATE OF CORRECTION

| | | |
|---|---|---|
| PATENT NO. | : 7,517,355 B2 | |
| APPLICATION NO. | : 11/222444 | |
| DATED | : April 14, 2009 | |
| INVENTOR(S) | : James Franklin Drake and Lynn R. Skow | |

It is certified that error appears in the above-identified patent and that said Letters Patent is hereby corrected as shown below:

Tile page, under (57) Abstract, line 6, delete "tends"

Col. 1, line 16, delete "s"

Col. 2, line 29, delete "contract" and insert --contact--

Col. 3, line 27, delete "tends"

Col. 5, line 3, delete "a" and insert --a--

Col. 6, line 24, delete "agent" and insert --agents--

Col. 7, line 7, delete "yams" and insert --yarns--

Col. 9, line 11, after "particularly", insert --useful--

Col. 9, line 26, delete "eight" and insert --weight--

Col. 9, line 28, delete "have" and insert --has--

Col. 9, line 41, delete "Sephaex" and insert --Sephadex--

Col. 9, line 43, delete "cutoff molecular" and insert --molecular sieve cutoff values--

Col. 9, line 56, delete "was" and insert --when--

Col. 10, line 5, delete "or" and insert --of--

Signed and Sealed this
Fourteenth Day of June, 2011

David J. Kappos
*Director of the United States Patent and Trademark Office*